United States Patent [19]

James

[11] 4,425,332

[45] Jan. 10, 1984

[54] ANTACID COMPOSITION

[75] Inventor: Michael H. James, Flamstead, England

[73] Assignee: Beecham Group Limited, England

[21] Appl. No.: 77,196

[22] Filed: Sep. 20, 1979

[30] Foreign Application Priority Data

Sep. 21, 1978 [GB] United Kingdom ............... 37617/78

[51] Int. Cl.$^3$ ...................... A61K 37/48; A61K 31/10; A61K 33/06; A61K 33/08
[52] U.S. Cl. ........................................ 424/94; 424/35; 424/38; 424/37; 424/154; 424/156; 424/157
[58] Field of Search .................... 424/35, 38, 157, 94, 424/156, 154, 37

[56] References Cited

U.S. PATENT DOCUMENTS

| | | | |
|---|---|---|---|
| 2,926,121 | 2/1960 | Hobbs et al. | 424/35 |
| 3,253,988 | 5/1966 | Scott | 424/127 |
| 3,843,778 | 10/1974 | Diamond | 424/157 |

*Primary Examiner*—Frederick E. Waddell
*Attorney, Agent, or Firm*—Jacobs & Jacobs

[57] ABSTRACT

Antacid dosage units comprising a finely divided solid antacid such as aluminium hydroxide dispersed in a fondant confectionary base are provided. Each dosage unit is sealed against moisture evaporation and may include antibacterial or antifungal preservatives as well as humectants and other adjuvants.

7 Claims, No Drawings

ANTACID COMPOSITION

This invention relates to the field of orally administrable antacid compositions.

Oral antacid compositions are generally based on the salts, hydroxides or carbonates of aluminium, calcium or magnesium, alone or in combination, as active ingredients.

These substances are water insoluble and are usually formulated for oral administration as aqueous suspensions or as solid tablets, the latter being dispersible in water before administration or disintegrable, suckable or chewable in the mouth. However, some consumers, particularly those who are obliged to consume antacids frequently, find the taste and mouth-feel of these traditional products unpleasant. The texture has been described as "gritty" or "chalky". The aim of the present invention is to provide an antacid composition which has a mouth-feel and texture different from the traditional compositions, and which is generally more pleasant to, and better tolerated by, many consumers.

According to the present invention there is provided a shaped antacid composition comprising an antacid compound in combination with a fondant confectionery base. Preferably, the antacid is in the form of a finely divided solid. The antacid may be combined with the base in various ways. For example, it may be dispersed in the base, or it may be formed as a liquid suspension or gel in the centre of the base, similar to a soft centred sweet.

The antacid may also be incorporated in an edible coating or incorporated in a third intermediate vehicle which can form a separate layer or phase in the fondant base. For example, the antacid could be suspended or encapsulated in a number of small globules of fat or gelatin and mixed into the fondant rather like raisins in a cake.

The antacid can be present in widely varying amounts, but the preferred content is from 4% to 25% by weight of the composition. The water content of the composition of the invention is preferably from 6% to 15% by weight.

The composition of the invention may be utilised in a variety of shaped forms. For example, it may take the form of a strip or bar, similar to a conventional chocolate bar. The user can then break off the required amount and retain the remainder for later use.

Preferably, the composition is provided in dosage unit form, sized for oral consumption, and the amount of antacid in each unit dose may be from 200 mg to 1200 mg.

The shaped composition of the invention may be manufactured by introducing a fondant mix containing the antacid into suitably shaped moulds. According to a further aspect of the invention, therefore, there is provided a fondant mix comprising an antacid compound in combination with a fondant confectionery base.

Fondant confectionery base has long been known and many recipes and processes for its preparation are known. In broad terms, a fondant confectionery base can be defined as a two-phase system between solid sugar particles and a dissolved sugar liquid phase. It characteristically contains a high proportion of tiny sucrose crystals (65% to 90% by weight) as a homogeneous dispersion in water (about 8% to 17% by weight) with small quantities of other carbohydrates such as dextrose, levulose, maltose, lactose, dextrins, glucose (solids or syrup) and invert sugar. Traditionally it may be prepared by dissolving sugar, glucose and invert sugar in water and concentrating to a supersaturated solution containing, say, 12% water. The supersaturated solution is cooled with vigorous beating or mixing and the sugar crystallises as tiny crystals in the liquid phase. The preparation of fondant base is, of course, well understood by those skilled in the art.

The antacid may be an aluminium, magnesium or calcium antacid, such as aluminium hydroxide or calcium carbonate.

The antacid adjuvants, sugar and other carbohydrates can be heated in water to a temperature of 70° to 130°, usually about 70° C. to 80° C., until the water content of the composition is from 13% to 18%, e.g. about 15%. It may then be allowed to cool with vigorous beating or stirring, to about 30° C. to 40° C., when the antacid is stirred in and the mixture is then poured into moulded impressions in a starch bed or rubber mould to complete the cooling. Further water is lost up to about 5%, leaving the final dosage units containing 8% to 12% water. The fondant sugar base may also be prepared by the well-known "bob" process, involving the boiling-down of the moisture content of the fondant mass to the desired level. The antacid ingredients are blended in after cooling to 60° C. and the mix poured into moulds to set. Alternative suitable drying processes could be used in place of or in addition to starch or rubber moulding.

Alternatively, the antacid and antacid adjuvants can be dry blended with fondant icing sugar in the desired ratio, added to the liquids and the liquid dispersion poured into moulds to dry and set.

Usually it is not desirable to add more than about 15% by weight of water to the dry mix. Drying and setting is accelerated if the liquid mix is heated to, say, 35° to 50° C. before pouring into the moulds.

The final dosage units are sized for oral consumption, and their fondant texture provides melt-in-the-mouth qualities. They may, therefore, be shaped like sweets. They may typically be similar in form to the confectionery products of the fondant mint and fondant cream or chocolate cream types. Flavourings may be included, particularly peppermint flavouring, which is sufficiently "strong" to counteract any residual taste of antacid not masked by the fondant base. Colouring may also be included if desired.

Other adjuvants may be added as necessary. These may include aeration aids, such as egg frappe, additional invert sugar, sugar hydrolysing enzymes or enzyme concentrates, and humectants which, by reducing or avoiding hardening, assist in keeping the product. The proportion of enzyme is preferably at least 0.1% of the composition, suitably from 0.1% to 1% of the composition. Examples of humectants are sorbitol and glycerol. An antibacterial or antifungal preservative, such as esters of para-hydroxy benzoate, may be included in the product of invention to protect it from microbial spoilage.

Preferably each dosage unit is sealed against evaporation of moisture, which tends to spoil the fondant texture. Thus the dosage units may be coated with an edible film designed to reduce or prevent moisture loss, for example, a vegetable or animal fat material, or chocolate or hard sugar, or may be individually wrapped or sealed in an inedible packaging film such as metal foil or metal/polymer laminate, or polymer material having suitable barrier properties.

The following Examples illustrate the preparation of antacid dosage units in accordance with the invention:

EXAMPLE 1

Dosage unit forms of 4.99 g each are prepared from a composition of 499 g containing the following quantities of ingredients.

| Formula | Weight (g) | % w/w |
| --- | --- | --- |
| Castor Sugar (ex Tate and Lyle) | 105.0 | 21.0 |
| Liquid Glucose 42D (SO$_2$ grade) (ex CPC) | 45.0 | 9.0 |
| White Fondant (ex Unecol) | 249.0 | 50.0 |
| Calcium Carbonate (Sturcal L) (ex Sturge Ltd) | 49.8 | 10.0 |
| Aluminium Hydroxide FMAS Reductionised (ex Reheis) | 24.9 | 5.0 |
| Peppermint Oil BP | 0.5 | 0.01 |
| Tartrazine | 0.004 | 0.0008 |
| Green S 12947 (ex Anstead) | 0.0004 | 0.00008 |
| Water | 25.0 | 5.0 |
|  | 499 g | 100.01% |

A fat coating of Kaomel (supplied by Durkee Industrial Foods) or Nucoa S (supplied by Loders-Nucolme Ltd) is applied to each unit to give the finished dosage unit form.

Method of Manufacture

The method is adapted from the common 'bob' process. An aqueous solution of glucose and castor sugar is prepared and after boiling off some water the resultant syrup is mixed with the white fondant at 60° C. The powdered active ingredients are then thoroughly mixed in, followed by the colour and flavour. The homogeneous mix is piped at 65° C. into rubber moulds and allowed to set. The fondant cores are fat coated in a suitable enrober, and after setting are packed. Further details of the steps in the method are given as follows in process steps (A) to (H):

(A) Preparation of Glucose/Sugar Syrup

|  | for 499 g |
| --- | --- |
| Castor Sugar | 105 g |
| Glucose 42D | 45 g |
| Water | 50 g |
|  | 200 g |

The syrup is boiled down to 171 g.

The sucrose, glucose and water are mixed by hand in a suitable vessel (beaker or household pan). The mixture is then heated gently until the sucrose has dissolved, it is then heated more strongly and boiled to reduce the water content to the correct level. When the syrup has reached the desired weight it is removed from the heat and allowed to cool to 60° C.

(B) Preparation of Unecol White Fondant (Raw Material)

The Unecol white fondant is melted by heating to 60° C.

(C) Preparation of the Active Ingredient Powder Premix

|  | for 499 g |
| --- | --- |
| Calcium Carbonate Sturcal L | 49.8 g |
| Aluminium Hydroxide FMA5 | 24.9 g |
|  | 74.7 g |

The aluminium hydroxide and the calcium carbonate are screened through a 355 N (IN) mesh. The appropriate quantities are added to a suitable blender and adequately mixed.

(D) Preparation of Core Colouring Solution

A final solution is made up as follows:

|  | % w/v |
| --- | --- |
| Tartrazine | 0.1 |
| Green S | 0.01 |
| Water | 100.0 |

4.0 ml of this solution is used for 499 g of the composition.

(E) Preparation of Final Fondant Cream Mix

|  | for 499 g |
| --- | --- |
| Syrup from process step (A) | 171.0 g |
| White fondant from process step (B) | 249.0 g |
| Active ingredient premix from process step (c) | 74.7 g |
| Colouring solution from process step (D) | 4.0 g |
| Peppermint oil | 0.5 g |
|  | 499.2 g |

The syrup is added to the white fondant, and the resultant cream is well mixed at 60° C. The active ingredient premix is then added. The actives often form lumps in the mixture, these must be removed by thorough mixing.

The colouring solution and the peppermint oil are then added with further stirring until homogeneous.

(F) Moulding and Setting of Fondant Cores

It has been found that the fondant mix is piped into the moulds more easily if it is heated to 65° C. before piping. Once this is done the fondant mix must be transferred to the moulds rapidly before setting occurs. A normal icing bag is used to pipe the fondant into rubber moulds. The cores set in ½ to ¾ of an hour when they can be pushed out of the moulds from behind.

(G) Preparation of Fat Coating Mix

| Fat Coat (Nucoa S or Kaomel) | } |  |
| --- | --- | --- |
| Peppermint Oil |  | q.s. |
| *Colouring |  |  |

*The colouring aluminium lakes of Green S and tartrazine are added to the fat in solid form.

The fat is shredded or broken up into small pieces. The fat is then gently heated with continuous stirring to 29° C. to 30° C.

At this point, the peppermint oil and colouring are added with mixing until a homogeneous mixture is obtained.

(H) Fat Coating

The coating is applied by dipping the fondants into the mix at 30° C. The fondants are then allowed to set on a suitable tray. Setting time is about 5 mins.

An 'enrober' may be used in manufacture, as this will control the thickness of the coat better than by hand. Other large scale techniques for applying fat or chocolate coats may also be used.

EXAMPLE 2

| Formula | % w/w |
|---|---|
| Sucrose | 65.42 |
| Dextrose Monohydrate | 8.17 |
| Aluminium Hydroxide Dried Gel | 10.00 |
| Flavour and Colour | q.s. |
| Water | to 100 |

Method of Manufacture

The water and sucrose are heated to boiling, when dextrose monohydrate is added. Heating is continued until the mixture boils at the specified temperature, calculated from the total solids content. In this case the boiling temperature is 115.7° C. As the mixture approaches that temperature, water loss may be monitered by weighing the entire vessel and contents. After removing from the heat the aluminium hydroxide is added and the mixture poured onto a slightly damp pyrex slab, where it is worked with a flexible spatula in a circular motion, and the peppermint oil is added at this stage. When crystallisation is complete, the mixture is kneaded for a few minutes before being shaped like sweets, and allowed to set to a water content of 8% to 12%. The individual units are then wrapped to protect from evaporation.

EXAMPLE 3

| Formula | % w/w |
|---|---|
| Fondant Icing (ex Tate and Lyle) | 74.3 |
| Aluminium Hydroxide Dried Gel | 10.0 |
| Magnesium Trisilicate | 1.0 |
| Colour and Flavour | q.s. |
| Water containing preservative | to 100 |

Method of Manufacture

The powdered ingredients, in this case Fondant Icing, Magnesium Trisilicate and Aluminium Hydroxide, are mixed and added to the water and dyes. Slight warming may be necessary. The flavouring is added last and the mixture is stirred until it becomes smooth and shiny, maintaining the temperature at around 40° C. The mixture is dispensed into moulds for setting to a moisture content of 8% to 12%. The units are then wrapped to protect from evaporation.

EXAMPLE 4

| Formula | % w/w |
|---|---|
| Fondant Icing (ex Tate and Lyle) | 67.3 |
| Aluminium Hydroxide FMA5 | 11.0 |
| Sorbitol Solution | 11.0 |
| Colour and Flavour | q.s. |
| Water containing Nipasept preservative | to 100 |

Method of Manufacture

As in Example 2, premixing sorbitol solution with water and dyes.

EXAMPLE 5

As Example 1, except that the Aluminium Hydroxide FMA5 is omitted and is substituted by the same amount of white fondant.

EXAMPLE 6

As Example 1, except that invertase concentrate (q.s. between 0.1% and 1%) is added after peppermint oil at Stage E.

I claim:

1. A shaped antacid composition comprising a dispersion from 4 to 25% by weight of a finely divided solid aluminum, magnesium or calcium antacid in a base consisting essentially of a two-phase system of solid sugar particles and a saturated sugar solution, the water content of the composition being from 6 to 15% by weight.

2. A composition according to claim 1, in dosage unit form.

3. A composition according to claim 2 containing from 200 mg to 1200 mg of antacid per dosage unit.

4. A composition according to claim 1, which has an edible coating to reduce or prevent moisture loss.

5. A composition according to claim 4, in which the coating comprises a vegetable or animal fat material.

6. A composition according to claim 1, which includes a pharmaceutically acceptable antibacterial or antifungal preservative.

7. A composition according to claim 1, including a non-toxic, sugar hydrolysing enzyme or enzyme concentrate.

* * * * *